United States Patent [19]
Uick et al.

[11] Patent Number: 5,928,634
[45] Date of Patent: Jul. 27, 1999

[54] LIQUID INSECT BAIT

[75] Inventors: Heidi J. Uick, Racine, Wis.; Peter J. Schroeder, Winsor, United Kingdom

[73] Assignee: S. C. Johnson & Son, Inc., Racine, Wis.

[21] Appl. No.: 08/848,044

[22] Filed: Apr. 28, 1997

Related U.S. Application Data

[63] Continuation of application No. 08/370,046, Jan. 9, 1995, abandoned.

[51] Int. Cl.$^6$ .......................... A01N 25/02; A01N 41/04; A01N 43/56; A01N 59/14
[52] U.S. Cl. .......................... 424/84; 424/405; 424/657; 424/658; 424/659; 424/660; 426/1; 514/407; 514/710; 514/711; 514/738; 514/970
[58] Field of Search .................. 424/84, 405, 657–660; 426/1; 514/738, 407, 710, 711, 970

[56] References Cited

U.S. PATENT DOCUMENTS

| | | | |
|---|---|---|---|
| 1,989,981 | 2/1935 | Hamilton | 424/84 |
| 2,829,085 | 4/1958 | Gerber et al. | 514/177 |
| 3,632,759 | 1/1972 | Jameston et al. | 514/481 |
| 4,049,460 | 9/1977 | Broadbent | 424/84 |
| 4,160,824 | 7/1979 | Inazuka et al. | 424/84 |
| 4,310,985 | 1/1982 | Foster et al. | 43/131 |
| 4,812,309 | 3/1989 | Ong | 424/84 |
| 4,889,710 | 12/1989 | Hagarty | 424/84 |
| 4,988,510 | 1/1991 | Brenner et al. | 424/84 |
| 5,017,620 | 5/1991 | Grassman et al. | 514/698 |
| 5,110,591 | 5/1992 | Williams | 424/195.1 |
| 5,126,139 | 6/1992 | Geary | 424/410 |
| 5,292,533 | 3/1994 | McMahon et al. | 424/408 |
| 5,388,772 | 2/1995 | Tsau | 241/17 |
| 5,484,587 | 1/1996 | Branly et al. | 424/84 |
| 5,556,631 | 9/1996 | Kelley | 424/410 |

FOREIGN PATENT DOCUMENTS

| | | |
|---|---|---|
| 52 313 A1 | 11/1981 | European Pat. Off. |
| 212 226 A1 | 7/1986 | European Pat. Off. |
| 278 878 A1 | 2/1988 | European Pat. Off. |
| 417 896 A1 | 7/1990 | European Pat. Off. |
| 508 022 A1 | 12/1991 | European Pat. Off. |
| 56-022706 | 3/1981 | Japan. |
| 56-068601 | 6/1981 | Japan. |
| 57-115404 | 7/1982 | Japan. |
| 60-149510 | 8/1985 | Japan. |
| 61-069872 | 4/1986 | Japan. |
| 61-106505 | 5/1986 | Japan. |
| 61-243007 | 10/1986 | Japan. |
| 62-042904 | 2/1987 | Japan. |
| 62-042906 | 2/1987 | Japan. |
| 62-042911 | 2/1987 | Japan. |
| 5155706 | 6/1993 | Japan. |
| 5286810 | 11/1993 | Japan. |
| 1766347 | 10/1992 | U.S.S.R. |
| 1837058 | 8/1993 | U.S.S.R. |
| 2 141 931 | 1/1985 | United Kingdom. |
| 2 278 278 | 11/1994 | United Kingdom. |
| 91/00007 | 1/1991 | WIPO. |
| 91/01736 | 2/1991 | WIPO. |
| 92/13454 | 8/1992 | WIPO. |
| 92/14363 | 9/1992 | WIPO. |
| 93/02554 | 2/1993 | WIPO. |
| 95/24124 | 2/1995 | WIPO. |
| 95/31100 | 11/1995 | WIPO. |

OTHER PUBLICATIONS

Chemical Abstracts, vol. 127, No. 4, p. 258, abstract no. 46494h, 1997.
Kirk–Othmer, *Encyclopedia of Chemical Technology, Third Edition*, vol. 1, pp. 754–772 (1978).

*Primary Examiner*—John Pak

[57] ABSTRACT

A liquid bait for target insects and methods of attracting or controlling insects by means of its use. Sorbitol is dissolved in an amount of water sufficient to form an aqueous carrier. The dissolved sorbitol is in a concentration great enough to be effective as a humectant to retard drying of the liquid carrier. The liquid bait further includes at least one insect attractant that is dissolved, dispersed, suspended, or emulsified in the liquid carrier in an amount effective to attract the target insects. The insect attractant may include, in combination, sucrose, fructose, d-maltose, the lithium salt of saccharin, lithium chloride, and vitamins. The liquid bait also may include an effective amount of an insect control active ingredient selected from the group consisting of insecticides, insect growth regulators, chitin inhibitors, insect pathogens, insect-controlling materials derived from insect pathogens, and combinations thereof.

5 Claims, 1 Drawing Sheet

LIQUID INSECT BAIT

This is a continuation of application Ser. No. 08/370,046 filed Jan. 9, 1995, now abandoned.

FIELD OF THE INVENTION

This invention relates to insect baits in general and, particularly, to liquid insect baits having delayed drying times.

BACKGROUND ART

It is generally understood that there are advantages to a liquid preparation when making a bait for use with insects that prefer or even require their food to be in liquid form prior to ingestion or digestion. Commercially available liquid ant baits are familiar, such as the water and sucrose product sold under the name "Terro Ant Killer" by Senoret Chemical Co., Inc. of St. Louis, Mo. However, liquid and even moist baits tend to dry out when exposed to the air during use, losing their advantage.

Brenner et al., U.S. Pat. No. 4,988,510, address the general problem of drying. Brenner et al. disclose a semi-solid insect bait that includes one or more humectants formulated together with an attractant and an insecticide to create a deformable, hydrophilic gel matrix. Sugars, glycerol, and other polyhydroxy alcohols are cited as humectants useful in the bait for the purpose of drawing moisture from the air to allow the bait to remain pliable and relatively moist. The humectant is stated to be present in an "effective amount," which is defined as that amount necessary to achieve the intended result of the component. For humectants, Brenner et al. describe that amount as being 30–45%; on a dry weight basis.

The inclusion of sorbitol in an insect bait is relevant to the present invention, and the polyhydroxy alcohols, referred to as a class by Brenner et al., could include sorbitol. Furthermore, Hagerty, U.S. Pat. No. 4,889,710, and Inazuka et al., U.S. Pat. No. 4,160,824, specifically include sorbitol in the insect bait preparations they describe. However, the Brenner et al. bait is not liquid, and Hagarty and Inazuka et al. utilize sorbitol not as a humectant but, instead, as an emulsifier. In Hagarty, an aerosol foam is disclosed that is formed of a water soluble, film-forming polymer. An emulsifier is included to emulsify the film-forming polymer so that it will foam, and sorbitol derivatives are cited among the examples of useful emulsifiers. Emulsifier amounts in the Hagarty composition range from 0.01 to 5% by weight.

Inazuka et al. describe insect attractive compositions that, among other options, may be used in solutions or emulsions, if dissolved or dispersed in a suitable liquid carrier with the aid of an emulsifier, dispersing agent, or the like. Sorbitols are referred to generally as being among the suitable emulsifiers, spreading agents, and penetrants for use with the Inazuka et al. insect attractive compositions. The proposed amount of sorbitol is not specified, and one skilled in the art therefore would understand that a conventional or an effective amount is being referred to. The disclosure of Hagarty, cited above, shows that one skilled in the art would expect such emulsifiers to be effective in an amount between 0.01 to 5% by weight.

Sorbitol is a commercially available material and is on the market as an aqueous solution in a variety of concentrations for a variety of purposes. Thus, sorbitol is conventionally available for manufacturing and other purposes in an aqueous solution that is approximately 70% sorbitol by weight. Gerber et al., U.S. Pat. No. 2,829,085, is a further example of sorbitol solutions in concentrations relevant to the present invention. Gerber et al. describe a parenteral vehicle for therapeutic agents in which sorbitol is used to aid in the suspension of non-soluble therapeutic agents in injectable aqueous preparations. In Gerber et al., sorbitol is used in an amount sufficient to raise the specific gravity of the water solution in which it is dissolved until it is substantially equal to the specific gravity of the therapeutic agent that is be suspended within the injectable preparation. Weight percentages of 30.4% and 59.2% are cited in two examples given to show the application of the Gerber et al. invention to two different therapeutics.

Neither Hagarty, Inazuka et al., nor Gerber et al. utilize sorbitol for its humectant properties, nor are any of them concerned with strategies to delay the drying of their preparations.

SUMMARY OF THE INVENTION

The invention is summarized in that a liquid bait for target insects includes sorbitol dissolved in an amount of water sufficient to form an aqueous carrier. The dissolved sorbitol is in a concentration great enough to be effective as a humectant to retard drying of the liquid carrier. However, it is also in a concentration small enough that the liquid carrier remains liquid upon the addition of any attractants or other ingredients of the liquid bait. The liquid bait further includes at least one insect attractant that is dissolved, dispersed, suspended, or emulsified in the liquid carrier in an amount effective to attract the target insects.

An alternative embodiment of the invention is summarized in that the insect attractant includes, in combination, sucrose, fructose, d-maltose, the lithium salt of saccharin, lithium chloride, and vitamins. This embodiment of the liquid bait also includes an effective amount of lithium perfluorooctane sulfonate as an insect control active ingredient.

The method of the invention is summarized in that a method of attracting target insects includes the step of exposing to the insects the liquid bait first summarized above. The method of the invention for controlling the target insects includes exposing to the insects that same liquid bait with the addition of an effective amount of an insect control active ingredient selected from the group consisting of insecticides, insect growth regulators, chitin inhibitors, insect pathogens, insect-controlling materials derived from insect pathogens, and combinations thereof. In a preferred embodiment of the method of controlling target insects, the insect attractant of the liquid bait includes, in combination, sucrose, fructose, d-maltose, the lithium salt of saccharin, lithium chloride, and vitamins. The insect control active ingredient preferred in this embodiment is lithium perfluorooctane sulfonate.

DETAILED DESCRIPTION OF THE INVENTION

Figure 1:
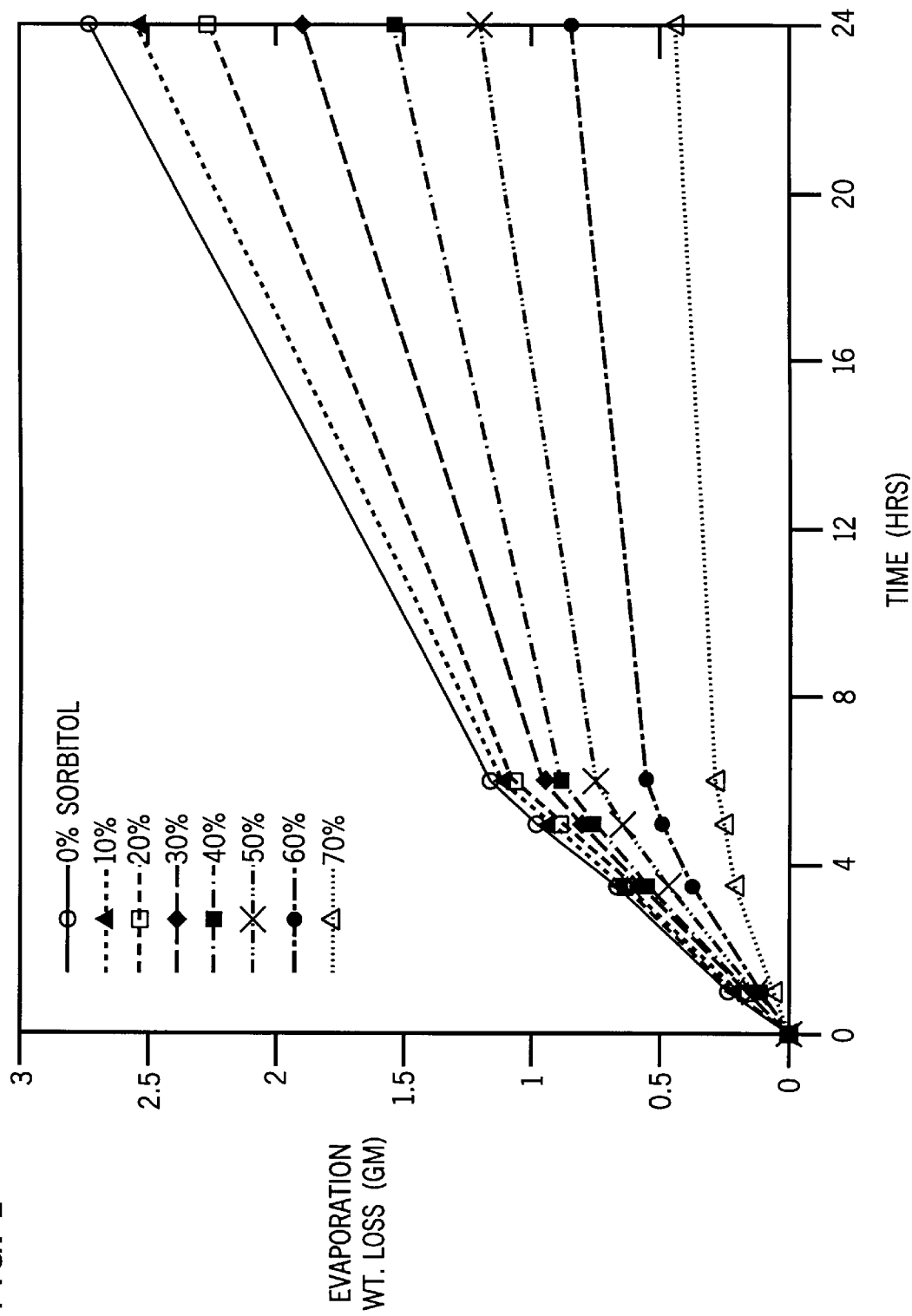
FIG. 1 is a graph showing the results of a measurement of the drying rates of differing concentrations of sorbitol in water.

The liquid bait for target insects of the invention has been so formulated as to provide an aqueous liquid carrier that has a slowed drying time. To achieve this end, an aqueous liquid carrier is made by dissolving sorbitol in water at a concentration great enough to be effective as a humectant, to retard drying of the aqueous liquid carrier. An "effective amount" of a component is defined as that amount capable of achieving the intended result of the component. As is shown in the examples, below, a minimal concentration of 20% sorbitol dissolved in water retards drying of the solution to an extent that is of interest for the liquid insect bait of the present invention.

Sorbitol is not itself effective as an attractant for insects. Therefore, at least one insect attractant must be carried by the aqueous liquid carrier in an amount effective to attract the target insects. For the insect attractant to be distributed through the liquid bait, it is necessary that the insect attractant either be dissolved, dispersed, suspended, or emulsified in the liquid carrier.

As the aqueous liquid carrier dries, an insect attractant that is dissolved therein normally will reach saturation and then begin to appear in solid form. Similarly, insect attractants that are dispersed, suspended, or emulsified will lose their ability to remain distributed through the liquid carrier or, alternatively, the entire preparation may dry to a paste and eventually even to a solid. Sorbitol, as one of the solids in solution in the aqueous liquid carrier, contributes to the total concentration of solids dissolved or otherwise carried within the liquid carrier. As a consequence, while the sorbitol dissolved in the aqueous liquid carrier must be in a concentration great enough to be effective as a humectant to retard drying, the concentration must also be small enough that the liquid carrier remains liquid upon the addition of desired amounts of the insect attractants or other ingredients of the liquid bait.

In theory, a very small amount of sorbitol could be dissolved in the liquid carrier, the water of which would then begin to evaporate. Upon continued evaporation of the water, the concentration of sorbitol would increase, along with that of the other dissolved materials. The humectant characteristics of the sorbitol would increase as it became more concentrated, causing the sorbitol to eventually significantly retard the drying of the bait. However, from a practical standpoint, the initial concentrations of sorbitol and the other ingredients dissolved, dispersed, suspended, or emulsified in the liquid carrier must be such that the liquid bait has useful function immediately and also does not lose an excessive percentage of its volume before the concentration of sorbitol is high enough to retard further drying. The minimal initial dry weight percent of sorbitol in the liquid bait of the invention is not less than 20%, preferably not less than 35%, and even more preferably is not less than 50%. The maximum dry weight percent of sorbitol that is preferred for practical purposes is 65%, and even more preferably is not more than 60%.

The insect attractant of the liquid bait of the invention may be selected from insect-attractive pheromones and scents and from insect-attractive ingestable materials, such as carbohydrates, proteins, fats, oils, inorganic salts, artificial sweeteners, vitamins, natural and artificial flavors, and any other attractant that can be carried by an aqueous liquid carrier and made accessible to insects feeding on the bait.

For any given target insect, a combination of attractants may be as or even more effective than the attractants individually. Thus, when the target insects are hymenopteran insects, it was found that a combination of sucrose, fructose, and d-maltose attracted the insects. Saccharin or alkali metal salts of saccharin also were found to be attractive. Sodium chloride and lithium chloride also are attractants, as are vitamins that can be dissolved or otherwise distributed through the aqueous liquid carrier. It was found that various combinations of these separately attractive insect attractants achieved optimal results. Furthermore, the mixture of naturally occurring sugars isolated from maize was also useful, being primarily composed of fructose but also having significant fractions of dextrose and higher saccharides.

The preferred embodiment of the liquid bait, especially when the target insects are ants or other hymenopteran insects, includes an insect attractant combining sucrose, fructose and d-maltose. Even more preferred is an insect attractant that also includes an alkali metal salt of saccharin and an alkali metal chloride. The best results were obtained when the insect attractant further included vitamins. Dr. Frantisek Sehnal of the Entomological Institute of the Czechoslovak Academy of Sciences reported in a public oral presentation in Racine, Wis., on Jun. 21, 1991, that poultry vitamins had proved attractive to insects in certain solid or semi-solid baits otherwise different from the liquid bait of the invention. Water soluble or dispersible vitamin preparations are preferred, although, the use non-water soluble vitamins as insect attractants is also possible, when the vitamins are made a part of an emulsion or other means of dispersing the vitamins throughout the aqueous liquid carrier of the invention. Such use and materials are also within the scope and spirit of the present invention.

The liquid baits described above, including those noted as preferred for ants and other hymenopteran insects, also have been found to be effective with othopteran insects. They also are believed to be effective for dermapteran, thysanuran, and other insects. Therefore, the scope of the present invention should not be understood as limited to any specific insect or order.

Liquid baits for insects can be useful in any of a number of circumstances without any insect control active ingredient. Thus, for research or insect population monitoring purposes or even for insect control, it may be useful to bait target insects to a trap or a feeding station where they may be held, observed, or counted, without the addition to the bait of materials that would further biologically affect the insects. However, it is common to include an insect control active ingredient in a bait in order to kill or otherwise regulate or biologically affect the insects. Thus, a preferred embodiment of the liquid bait of the invention includes an effective amount of an insect active control ingredient that may be dissolved, dispersed, suspended, or emulsified in the liquid carrier in an amount effective to achieve the result desired with respect to insects feeding on the liquid bait. The preferred insect control active ingredients of the invention are selected from the group consisting of insecticides, insect growth regulators, chitin inhibitors, insect pathogens, insect controlling materials derived from insect pathogens, and combinations thereof.

Various insecticides are available and appropriate for use with the liquid bait of the invention. To be useful in the invention, an insecticide must not be so repelling to the target insect that the insect fails to feed on the liquid bait, and the insecticide must also be capable of being dissolved, dispersed, suspended, or emulsified in the liquid carrier in a concentration effective to achieve the desired results. Even relatively small concentrations of insecticides nevertheless may be effective if the insecticide is itself very potent in small quantities or if slow or cumulative action is desired so that an insect may feed repeatedly on the bait before its death. The latter is commonly a goal when it is desired to induce a social insect to repeatedly carry an active ingredient into its nest so that not just the initially feeding insect but also the entire nest can be affected by the active ingredient.

Useful, presently available insecticides include but are not limited to organo-phosphates such as chlorpyrifos, phoxim, and acephate; non-phosphate insecticides such as hydramethylnon; inorganic insecticides such as boric acid, sodium borate, and silica aerogel; pyrethrum and synthetic pyrethroids such as transfluthrin, cyfluthrin, deltamethrin, d-phenothrin, and fenvalerate; carbamates such as propoxur, carbaryl, bendiocarb, fenoxycarb, and dioxycarb; pyrazoles such as fipronil sold by Rhone-Poulenc Ag Co. of Research Triangle Park, N.C.; pyrroles such as the product sold as "Pirate" by American Cyanamid Co. of Wayne, N.J.; sulfonates and related insecticides such as lithium perfluorooctane sulfonate and N-ethyl perfluorooctanesulfonamide; and cyclocompounds such as lindane, aldrin, dieldrin, and endrin.

Useful insect growth regulators include but are not limited to methoprene, fenoxycarb, and pyriproxyfen. Chitin inhibitors include but are not limited to flufenoxuron (sold as "Motto" by the Shell Chemical Company of Houston, Tex.) and lufenuron (as sold by the Ciba-Geigy Corp. of Greensboro, N.C.).

Living insect pathogens, such as insect pathogenic viruses, bacteria, fungi, or nematodes, also may be delivered to a target insect by inclusion in the liquid bait of the invention. Examples include strains of Baculovirus, other useful bacteria such as strains of *Bacillus thuringiensis* and *Bacillus sphaericus*, strains of the fungus Verticillium, and naturally occurring entomogenous nematodes, such as those sold under the mark "Biosafe" by Biosys, Inc. of Palo Alto, Calif. Alternatively, insect controlling materials may be derived or recovered from insect pathogens. Examples of such materials include the exotoxin crystals isolatable from *B. thuringiensis*; certain processed material from Xenorhabis spp. nematodes, and certain bacterial fermentation products such as avermectins and the product sold under the mark "DiBeta" by Abbott Laboratories of North Chicago, Ill. DiBeta, also known as "beta-exotoxin," is reported to be a biological insecticide derived from the bacterial fermentation of a strain of *B. thuringiensis*. All types of insect control active ingredients may be used individually or in combination with other, compatible insect control active ingredients.

A preferred insect control active ingredient includes an effective amount of lithium perfluorooctane sulfonate as an insecticide. Consequently, when the insect attractant includes a salt of saccharin, as is preferred, it is necessary that that salt be the lithium salt of saccharin, in order to avoid precipitation of the lithium perfluorooctane sulfonate. The lithium salt of saccharin may be prepared prior to formulation of the liquid bait, or it may be produced in situ by reacting saccharin and lithium carbonate as the bait is itself formulated.

The method of the invention for attracting target insects includes the step of exposing to the insects a liquid bait of the sort disclosed, above. The bait may be exposed in a cup or other container in which it may pool. However, in order both to avoid spillage and to further retard the drying of the liquid bait, it is preferred to contain the liquid bait within a spill-resistant container and to restrict the atmosphere's access to the liquid bait. Even a porous pellet, such as a compacted food pellet of the sort conventionally used for laboratory animals, can serve as a substrate into which the liquid bait can be allowed to soak, the body of the pellet itself serving as a reservoir from which the liquid bait wicks to the surface of the pellet to be exposed to insects.

The liquid insect bait of the invention can be prepared by conventional means of manufacturing liquid formulations. Suitable methods include cold blending and other mixing procedures generally available to those skilled in the art. Particular procedures for making liquid insect bait in accord with the invention when a lithium salt of saccharin is a desired ingredient are set forth below in the examples.

The liquid insect bait, the method of attracting target insects, and the method of controlling target insects of the invention will now be illustrated by way of the following examples, where all percentages are by dry weight and all temperatures are expressed in ° C. unless otherwise indicated. These are examples only and are not to be understood as limiting the scope of the invention.

EXAMPLE 1

Retardation of Evaporative Moisture Loss From Aqueous Liquid Preparations by Addition of Sorbitol FIG. 1 is a graph that shows the results of a measurement of the drying rates of aqueous solutions of sorbitol. Solutions of sorbitol in deionized water were prepared containing from 0 to 70% sorbitol by dry weight, the solutions being prepared in 10% increments. Three gram samples of each solution then were placed in open weigh boats and exposed to the air for twenty-four hours, the experiment being run in triplicate. The boats and samples were weighed initially, and evaporative moisture loss was monitored by periodic subsequent weighing at the times indicated on the graph.

In general, the retardation of drying increased with the concentration of sorbitol, with a 20% sorbitol concentration being the least concentration at which a weight loss rate different from that of the solution having 0% sorbitol was detectable with statistical significance at $p=0.05$, with analysis of variance by the Bonferroni test for multiple comparisons. This was deemed the minimal sorbitol concentration at which a practical advantage in the retardation of drying was obtained.

EXAMPLE 2

Manufacturing methods for certain preferred formulations of the insect bait of the invention The formulations of the liquid insect bait of the invention disclosed below were made in accord with the following processes. The sorbitol used was a commercial aqueous solution of sorbitol containing 70% sorbitol by dry weight. Cornsweet 95 is an aqueous preparation containing a mixture of soluble sugars isolated from maize, of which 95% is fructose. Cornsweet 95 contains approximately 23% water. These commercial aqueous preparations will be referred to respectively as "sorbitol, 70%" and "Cornsweet 95, 77%." Vitamin Mix F8095 is a water soluble vitamin mix for lepidoptera sold by Bio-Serv, a Holton Industries Company of Frenchtown N.J. Although Vitamin Mix F8095 was used, other vitamin preparations utilizable by insects could be substituted therefor. The commercial d-maltose preparation used was 90% d-maltose, 10% other dry materials and will be referred to simply as "d-maltose." The water used was deionized.

Sample 1 was prepared by charging the sorbitol, 70% to a kettle. The sodium saccharin, sucrose, d-maltose, and Cornsweet 95, 77% were added and mixed until dissolved. The application of low heat (approximately 49° C.) hastened the process. The sodium chloride, Vitamin Mix F8095, and water were mixed in a second container and, once the solids were dissolved, the container's contents were added to the kettle. The contents of the kettle were mixed well, to complete the preparation of Sample 1.

For Sample 2, the sorbitol, 70% was charged to a kettle, and the sucrose, d-maltose and Cornsweet 95, 77% were added and mixed until fully dissolved. The application of low heat (approximately 49° C.) hastened the process. The saccharin and a portion of the water were mixed in a second kettle, the saccharin dispersing but not dissolving. The lithium carbonate was added to the second kettle and mixed, and a foaming reaction occurred. The contents of the second kettle were then added to the first kettle. The Vitamin F8095, lithium chloride, and the remaining water were mixed in a third kettle, generating some heat. After they had dissolved, the contents of the third kettle were added to the first kettle and mixed well, to complete the preparation of Sample 2.

For Samples 3–6, the sorbitol, 70% was charged to a kettle, followed by the sucrose, d-maltose, and Cornsweet 95, 77%. All of these were mixed until fully dissolved to produce a sorbitol intermediate mixture. The dissolving process was hastened by the application of low heat (approximately 49° C.). The saccharin and water were charged to a second kettle and mixed. The saccharin dispersed in the water but did not dissolve because saccharin is not water soluble. Then lithium carbonate was charged to the second kettle. A foaming reaction occurred as the lithium salt of saccharin was created, and the contents of the second kettle were mixed until the product was clear, to produce a lithium saccharin intermediate mixture. The contents of the second kettle were added to the sorbitol intermediate mixture of the first kettle.

For Samples 3–6, the lithium perflurooctane sulfonate was charged to a third kettle with water and mixed until dissolved. This solution was then added to the first kettle, now containing both the sorbitol and lithium saccharin intermediate mixtures. The ingredients of the first kettle were then again mixed thoroughly. Finally, the vitamins, lithium chloride, and additional water were placed in a fourth kettle and mixed to produce a vitamin/alkali metal salt intermediate mixture. Some heat was generated in the process. The vitamin/alkali metal salt intermediate mixture was mixed until dissolved and then was added to the contents of the first kettle to produce the final formulation. The entire batch was then mixed thoroughly.

Sample 7 was prepared by charging the sorbitol, 70% to a kettle, followed by the addition of the sucrose, d-maltose, Cornsweet 95, 77%, and sodium saccharin. These were mixed until dissolved, with low heat (49° C.) added to speed the process. In a second container, the sodium chloride and Vitamin Mix F8095 were mixed with water until dissolved and then were added to the kettle. A 1% solution of fipronil in N-methyl pyrrolidone was prepared. Appropriate amounts of this solution were added to achieve the desired concentration of fipronil in the final formulation, completing preparation of Sample 7.

Samples 8–10 were prepared in the same manner as Sample 7, except that no sodium saccharin was added to the kettle and, instead of the fipronil solution, a water solution of boric acid was prepared and used in amounts sufficient to achieve the desired concentration of boric acid in the sample.

Sample 11 was prepared by adding the sorbitol, 70% to a kettle, followed by the sucrose, d-maltose, Cornsweet 95, 77%, and sodium saccharin, all of which was mixed at about 49° C. until dissolved. In a second container, the sodium chloride and Vitamin Mix F8095 were dissolved in water and then added to the kettle. The sodium borate was then added to the kettle and mixed until fullly dissolved, to complete preparation of Sample 11.

In Table 1, the formulations are expressed in terms of the percentages of the commercial ingredients used, in the form identified, above. In Table 2, the same formulations are described in terms of the calculated dry weight percentage of each ingredient. Likewise, in Table 3, the formulations are expressed in terms of the percentages of the commercial ingredients used, in the form identified, above. In Table 4, the same formulations as disclosed in Table 3 are described in terms of the calculated dry weight percentage of each ingredient.

TABLE 1

| Chemical Name | Sample 1 Na Base | Sample 2 Li Base | Sample 3 Li Base 0.5% Active | Sample 4 Li Base 1% Active | Sample 5 Li Base 2% Active | Sample 6 Alt. Li Base 1% Active |
|---|---|---|---|---|---|---|
| Water | 3.320 | 6.000 | 6.000 | 6.000 | 8.000 | 4.500 |
| Sorbitol, 70% | 80.000 | 77.155 | 76.655 | 76.155 | 73.155 | 79.420 |
| Sucrose | 5.000 | 5.000 | 5.000 | 5.000 | 5.000 | 5.000 |
| Cornsweet 95, 77% | 6.700 | 6.700 | 6.700 | 6.700 | 6.700 | 6.700 |
| d-Maltose | 3.200 | 3.200 | 3.200 | 3.200 | 3.200 | 3.200 |
| Saccharin, Na Salt | 1.000 | | | | | |
| Saccharin | | 0.969 | 0.969 | 0.969 | 0.969 | |
| Lithium Carbonate | | 0.196 | 0.196 | 0.196 | 0.196 | |
| Sodium Chloride | 0.600 | | | | | |
| Lithium Chloride | | 0.600 | 0.600 | 0.600 | 0.600 | |
| Vitamin Mix F8095 | 0.180 | 0.180 | 0.180 | 0.180 | 0.180 | 0.180 |
| Lithium Perfluoro- octane Sulfonate | | | 0.500 | 1.000 | 2.000 | 1.000 |
| Total: | 100.000% | 100.000% | 100.000% | 100.000% | 100.000% | 100.000% |

TABLE 2

| Chemical Name | Sample 1 Na Base No Active | Sample 2 Li Base No Active | Sample 3 Li Base 0.5% Active | Sample 4 Li Base 1% Active | Sample 5 Li Base 2% Active | Sample 6 Alt. Li Base 1% Active |
|---|---|---|---|---|---|---|
| Water | 28.861 | 30.688 | 30.538 | 30.388 | 31.488 | 29.867 |
| Sorbitol, dry | 56.000 | 54.008 | 53.658 | 53.308 | 51.208 | 55.594 |
| Sucrose | 5.000 | 5.000 | 5.000 | 5.000 | 5.000 | 5.000 |
| Cornsweet 95, dry | 5.159 | 5.159 | 5.159 | 5.159 | 5.159 | 5.159 |
| d-Maltose | 3.200 | 3.200 | 3.200 | 3.200 | 3.200 | 3.200 |
| Saccharin, Na Salt | 1.000 | | | | | |
| Saccharin | | 0.969 | 0.969 | 0.969 | 0.969 | |
| Lithium Carbonate | | 0.196 | 0.196 | 0.196 | 0.196 | |
| Sodium Chloride | 0.600 | | | | | |
| Lithium Chloride | | 0.600 | 0.600 | 0.600 | 0.600 | |
| Vitamin Mix F8095 | 0.180 | 0.180 | 0.180 | 0.180 | 0.180 | 0.180 |
| Lithium Perfluorooctane Sulfonate | | | 0.500 | 1.000 | 2.000 | 1.000 |
| Total: | 100.000% | 100.000% | 100.000% | 100.000% | 100.000% | 100.000% |

TABLE 3

| Chemical Name | Sample 7 0.001% Fipronil | Sample 8 2% Boric Acid | Sample 9 3% Boric Acid | Sample 10 5% Boric Acid | Sample 11 3% Na Borate |
|---|---|---|---|---|---|
| Deionized Water | 3.317 | 3.000 | 3.000 | 3.000 | 3.220 |
| Sorbitol, 70% | 79.920 | 79.320 | 78.320 | 76.320 | 77.600 |
| Sucrose | 4.995 | 5.000 | 5.000 | 5.000 | 4.850 |
| Cornsweet 95, 77% | 6.693 | 6.700 | 6.700 | 6.700 | 6.499 |
| d-Maltose | 3.197 | 3.200 | 3.200 | 3.200 | 3.104 |
| Saccharin, Na Salt | 0.999 | | | | 0.970 |
| Sodium Chloride | 0.599 | 0.600 | 0.600 | 0.600 | 0.582 |
| Vitamin Mix F8095 | 0.180 | 0.180 | 0.180 | 0.180 | 0.175 |
| N-Methyl Pyrrolidone | 0.099 | | | | |
| Fipronil | 0.001 | | | | |
| Sodium Borate | | | | | 3.000 |
| Boric Acid | | 2.000 | 3.000 | 5.000 | |
| Total: | 100.000 | 100.000 | 100.000 | 100.000 | 100.000 |

TABLE 4

| Chemical Name | Sample 7 0.001% Fipronil | Sample 8 2% Boric Acid | Sample 9 3% Boric Acid | Sample 10 5% Boric Acid | Sample 11 3% Na Borate |
|---|---|---|---|---|---|
| Water | 28.832 | 28.337 | 28.037 | 27.437 | 27.995 |
| Sorbitol, dry | 55.944 | 55.524 | 54.824 | 53.424 | 54.320 |
| Sucrose | 4.995 | 5.000 | 5.000 | 5.000 | 4.850 |
| Cornsweet 95, dry | 5.154 | 5.159 | 5.159 | 5.159 | 5.004 |
| d-Maltose | 3.197 | 3.200 | 3.200 | 3.200 | 3.104 |
| Saccharin, Na Salt | 0.999 | | | | 0.970 |
| Sodium Chloride | 0.599 | 0.600 | 0.600 | 0.600 | 0.582 |
| Vitamin Mix F8095 | 0.180 | 0.180 | 0.180 | 0.180 | 0.175 |
| N-Methyl Pyrrolidone | 0.099 | | | | |
| Fipronil | 0.001 | | | | |
| Sodium Borate | | | | | 3.000 |
| Boric Acid | | 2.000 | 3.000 | 5.000 | 3.000 |
| Total: | 100.000 | 100.000 | 100.000 | 100.000 | 100.000 |

EXAMPLE 3

Preferred, "two kettle" manufacturing process

Although the four kettle process of Example 2 was in fact used for preparation of lithium perfluorooctane sulfonate materials such as Samples 3–6 for laboratory testing purposes, an example of a simplified and preferred method of manufacture is as follows, referring to the commercial form of the ingredients, described in Example 2.

In a first kettle, a first intermediate was made having the following ingredients: deionized water 42.03%, lithium carbonate 2.08%, saccharin 10.18%, lithium chloride 6.31%, Vitamin Mix F8095 1.90%, and lithium perfluorooctane sulfonate 37.53%. The first intermediate was prepared by the following procedure:

The water was placed in the kettle and agitation was begun. Next the lithium carbonate was added and agitated until dissolved. Next the saccharin was added, one forth at a time to prevent excessive foaming. Agitation was increased to create a vortex, with agitation continued after each addition of saccharin until foaming had dissipated and the saccharin was dissolved. Agitation was continued for five minutes after the final addition of saccharin. Next, the lithium chloride was added, and the mixture was agitated until the solution was clear. Then the vitamin mixture was added and mixed until clear. Finally, the lithium perfluorooctane sulfonate was added and mixed for two minutes.

In a second kettle, a second intermediate was prepared including the following ingredients: sorbitol, 70%: 75.584%; sucrose 5%, Cornsweet 95, 77%: 6.7%; d-maltose: 3.2%. The second intermediate was prepared by the following procedure:

First the sorbitol, 70% was charged to the kettle and agitation was begun. The kettle was heated to about 38–43° C. Next the Cornsweet 95, 77% was added and allowed to mix thoroughly with the sorbitol, 70%. Next the sucrose was added, and the mixture was agitated until clear. Finally, the d-maltose was added, and the mixture was agitated for an additional five minutes to create the second intermediate.

To produce the final formulation, the first intermediate was added to the second intermediate and mixed for five minutes.

The following experiments were conducted to demonstrate the baiting characteristics of the indicated formulations:

EXPERIMENT 1

Feeding Tests: Ants

In separate tests, Pharaoh's Ants (*Monomorium pharaonis*) were allowed to select among simultaneously presented, aqueous liquid insect baits. The purpose was to verify that the ants would feed on the baits and to establish the relative effects of the various combinations of attractants. The baits were all generally similar in formulation, except that the insect attractants varied as indicated in the table, below. Consumption was measured by detecting weight loss. "Sorbitol" is sorbitol, 70%. "NaSaccharin" is the sodium salt of saccharin. "Sugar" refers to a mixture of d-maltose, Cornsweet 95, 77%, and sucrose. "BSA" is bovine serum albumin, and "vitamin" is Vitamin Mix F8095.

| SAMPLE DESCRIPTION | (gm) CONSUMPTION | % of TOTAL CONSUMPTION |
|---|---|---|
| TEST 1: | | |
| Sorbitol | 0.1372 | 1.22 |
| Sorbitol/Sugars | 5.0534 | 45.13 |
| Sorbitol/NaSaccharin | 1.0117 | 9.03 |
| Sorbitol/NaSaccharin/NaCl | 1.2550 | 11.21 |
| Sorbitol/NaSaccharin/Vitamin | 1.4222 | 12.70 |
| Sorbitol/NaSaccharin/NaCl/Vitamin | 2.3133 | 20.70 |
| Total: | | 100 |
| TEST 2: | | |
| Sorbitol | 0.6561 | 11.30 |
| Sorbitol/Sucrose | 1.1499 | 19.80 |
| Sorbitol/Sugars | 0.6722 | 11.60 |
| Sorbitol/Sugar/NaSaccharin | 0.7815 | 13.40 |
| Sorbitol/Sugars/NaCl/Vitamin | 1.2454 | 21.40 |
| Sorbitol/Sugars/NaSaccharin/NaCl/Vitamin | 1.3073 | 22.50 |
| Total: | | 100 |
| TEST 3: | | |
| Round A | | |
| Sorbitol/Sucrose/NaCl/Vitamin | 3.9343 | 40.40 |
| Sorbitol/Sugars/NaSacc/NaCl/Vitamin | 3.9951 | 41.00 |
| Sorbitol/Sucrose/NaCl/Vitamin/BSA | 1.8081 | 18.60 |
| Total: | | 100 |
| Round B | | |
| Sorbitol/Sucrose/NaCl/Vitamin | 4.0385 | 33.70 |
| Sorbitol/Sugars/NaSacc/NaCl/Vitamin | 6.0421 | 50.50 |
| Sorbitol/Sucrose/NaCl/Vitamin/BSA | 1.8938 | 15.80 |
| Total: | | 100 |
| Round C | | |
| Sorbitol/Sucrose/NaCl/Vitamin | 0.1350 | 10.60 |
| Sorbitol/Sugars/NaSacc/NaCl/Vitamin | 1.0143 | 79.50 |
| Sorbitol/Sucrose/NaCl/Vitamin/BSA | 0.1270 | 9.90 |
| Total: | | 100 |
| Round D | | |
| Sorbitol/Sucrose/NaCl/Vitamin | 0.0268 | 6.00 |
| Sorbitol/Sugs/NaSacc/NaCl/Vitamin | 0.3754 | 84.00 |
| Sorbitol/Sucrose/NaCl/Vitamin/BSA | 0.0448 | 10.00 |
| Total: | | 100 |

EXPERIMENT 2

Feeding Test: Yellow Jacket Wasps

Wasps (*Vespula germanica* and *V. maculifrons*) were exposed individually for two hours either to a liquid insect bait comparable to Sample 1 of Example 2 or to a 40 weight percent solution of sucrose. Eight replications were run for each test situation set forth in the table, below. Consumption was measured in $\mu l$, corrected for evaporation (the sucrose solution evaporating more rapidly than the sorbitol containing bait). When "starvation" is indicated, the wasps were isolated from food for the indicated time periods prior to the test exposure to the bait and sucrose solutions. The experiment indicates that, while the wasps fed more extensively on the sucrose solution, wasps do in fact feed on the sorbitol-containing liquid insect bait.

| | no starv | 2 hr starv | 4 hr starv |
|---|---|---|---|
| Liquid Insect Bait | 9.4 | 8.1 | 6.6 |
| 40% (wt/vol) Sucrose solution | 21.0 | 32.1 | 17.8 |

EXPERIMENT 3

Pharaoh's Ants: Colony kill test

A colony kill test was conducted using a sodium base bait comparable to Sample 7 of Example 2, with 0.001% fipronil. Total numbers of dead Pharaoh's Ants per nest were counted for 6 weeks, with 3 replicate colonies per test. The experiment indicates that exposing the ants to the liquid insect bait of the invention, including an insecticide as an insect control active ingredient, was effective in controlling ants.

| Treatment | Mean Dead Count |
|---|---|
| bait | 822.3 |
| control | 166.0 |

The observed difference was significant, as analyzed using a paired T-test (p=0.004).

EXPERIMENT 4

Population Monitoring Test: *B. germania* (German cockroach)

The cockroaches caught on sticky traps exposed for a 24 hour period were counted before and after availability of a porous rat food pellet material impregnated with the liquid insect bait of Sample 3 of Example 2. The figures represent the total insect catch on an array of four sticky traps in an apartment kitchen at a test site in the Czech Republic. The experiment indicates that exposing the roaches to the liquid insect bait of the invention, including an insecticide as an insect control active ingredient, was effective in controlling roaches.

Total Number of Roaches Caught on Four Traps

| Week of Trial (week 0 = BT, weeks 2ff = AT) | Males | Females | Nymyhs: Instar 3-7 | Nymphs: Instar 1-2 | Total | Reduction in % |
|---|---|---|---|---|---|---|
| 0 | 11 | 12 | 23 | 78 | 124 | |
| 2 | 2 | 2 | 5 | 11 | 20 | 83.9 |
| 3 | 0 | 0 | 2 | 4 | 6 | 95.2 |
| 4 | 2 | 1 | 4 | 1 | 8 | 94.5 |
| 6 | 0 | 0 | 0 | 0 | 0 | 100.0 |
| 8 | 0 | 0 | 0 | 0 | 0 | 100.0 |

"BT" and "AT" mean, respectively, before and after initiation of treatment.

"BT And AT" mean, respectively, before and after initiation of treatment.

EXPERIMENT 5

Colony Kill Tests

Liquid insect baits substantially the same as Samples 8–10 of Example 2 were presented to the insects of test colonies of Pharaoh's Ants, with each test condition run in quadruplicate. Ant populations were counted just prior to bait presentation and thereafter at weekly intervals. The normal diet under which the ants had been reared was used as a control. No controlling effect on the ants was observed, and the experiment was terminated at the end of the third week. It is unclear what these negative results indicate, if anything. They may indicate that boric acid as an insect control active ingredient is ineffective against ants under the conditions of the experiment. The results contrast with those of Experiment 3, in which fipronil was the insecticide used.

From an examination of the above specification and examples, those skilled in the art will be aware of modifications and variations of the invention immediately substitutable for the steps and materials disclosed. Such modifications and variations may fall within the scope and breadth of the invention. Therefore, the invention is not to be deemed limited except as set forth in the claims, below.

Industrial Applicability

As is discussed, above, insect baits in liquid form have advantages for use with insects requiring or preferring liquid food for ingestion or digestion. Such baits are industrially useful for insect monitoring and control in research, commercial, and domestic contexts. For such baits to be optimally useful, they must remain liquid for as long as possible. The present invention addresses that need for a liquid insect bait of retarded drying time.

We claim:

1. A liquid bait for target insects, comprising:

a. sorbitol dissolved in an amount of water sufficient to form an aqueous liquid carrier, the dissolved sorbitol being in a concentration great enough to be effective as a humectant to retard drying of the liquid bait and small enough that the liquid carrier remains liquid upon the addition of other ingredients of the liquid bait, wherein the dry weight percent of sorbitol is not less than 20% and not more than 60% of the bait;

b. at least one insect attractant dissolved, dispersed, suspended, or emulsified in the liquid carrier in an.amount effective to attract the target insects, wherein the attractant is selected from the group consisting of insect ingestible carbohydrates, saccharin, alkali metal salts of saccharin, alkali metal chlorides, vitamins, and combinations thereof; and c. an effective amount of an insect control active ingredient selected from the group consisting of insecticides, insect growth regulators, and chitin inhibitors, and wherein the insect control active ingredient is at least 0.001% by weight, and no more than the balance, of the bait.

2. The liquid bait of claim 1 wherein the dry weight percent of sorbitol of the bait is not less than 35% and not more than 60%.

3. The liquid bait of claim 1 wherein the dry weight percent of sorbitol of the bait is not less than 50% and not more than 60%.

4. The liquid bait of claim 1 wherein the liquid bait is held within a porous body as a reservoir for holding the bait.

5. A method of attracting target insects comprising the step of exposing to the insects a liquid bait including:

a. sorbitol dissolved in an amount of water sufficient to form an aqueous liquid carrier, the dissolved sorbitol being in a concentration great enough to be effective as a humectant to retard drying of the liquid bait and small enough that the liquid carrier remains liquid upon the addition of other ingredients of the liquid bait, wherein the dry weight percent of sorbitol of the liquid bait is not less than 20% and not more than 60% of the bait;

b. at least one insect attractant dissolved, dispersed, suspended, or emulsified in the liquid carrier in an amount effective to attract the target insects, wherein the attractant is selected from the group consisting of insect ingestible carbohydrates, saccharin, alkali metal salts of saccharin, alkali metal chlorides, vitamins, and combinations thereof; and c. an effective amount of an insect control active ingredient selected from the group consisting of insecticides, insect growth regulators, and chitin inhibitors, and wherein the insect control active ingredient is at least 0.001% by weight, and no more than the balance, of the bait.

* * * * *